US010577745B2

(12) United States Patent
Haraikawa et al.

(10) Patent No.: US 10,577,745 B2
(45) Date of Patent: Mar. 3, 2020

(54) TRANSFER PRINTING PAPER AND MANUFACTURING METHOD OF SMART FABRIC

(71) Applicant: Kinpo Electronics, Inc., New Taipei (TW)

(72) Inventors: Koichi Haraikawa, New Taipei (TW); Jen-Chien Chien, New Taipei (TW); Yin-Tsong Lin, New Taipei (TW); Tsui-Shan Hung, New Taipei (TW)

(73) Assignee: Kinpo Electronics, Inc., New Taipei (TW)

( * ) Notice: Subject to any disclaimer, the term of this patent is extended or adjusted under 35 U.S.C. 154(b) by 0 days.

(21) Appl. No.: 15/916,257

(22) Filed: Mar. 8, 2018

(65) Prior Publication Data
US 2019/0099994 A1 Apr. 4, 2019

(30) Foreign Application Priority Data

Oct. 3, 2017 (TW) .............................. 106134164 A

(51) Int. Cl.
*D06P 5/24* (2006.01)
*H05K 3/12* (2006.01)
*A61B 5/00* (2006.01)
*H05K 1/09* (2006.01)
*A61B 5/04* (2006.01)
*H05K 1/03* (2006.01)
*B41M 7/00* (2006.01)

(52) U.S. Cl.
CPC .............. *D06P 5/003* (2013.01); *A61B 5/04* (2013.01); *A61B 5/6804* (2013.01); *H05K 1/038* (2013.01); *H05K 1/095* (2013.01); *H05K 3/1275* (2013.01); *B41M 7/0027* (2013.01); *B41M 2205/10* (2013.01)

(58) Field of Classification Search
CPC .. A41D 1/00; A41D 1/002; A61B 5/04; A61B 5/6804; B41M 5/025; D06P 5/003
USPC ..................... 428/32.69, 32.74, 32.77, 32.81
See application file for complete search history.

(56) References Cited

U.S. PATENT DOCUMENTS

| 8,945,328 B2 * | 2/2015 | Longinotti-Buitoni ............... A61B 5/0002 156/234 |
| 2008/0057233 A1 * | 3/2008 | Harrison .............. B41M 5/3825 428/32.74 |
| 2015/0143601 A1 | 5/2015 | Longinotti-Buitoni et al. |

FOREIGN PATENT DOCUMENTS

| CN | 101535558 | 9/2012 |
| EP | 2196142 | 6/2010 |
| TW | M262032 | 4/2005 |
| TW | I536961 | 6/2016 |

(Continued)

OTHER PUBLICATIONS

"Search Report of Europe Counterpart Application", dated Jan. 21, 2019, p. 1-p. 9.

(Continued)

*Primary Examiner* — Gerard Higgins
(74) *Attorney, Agent, or Firm* — JCIPRNET

(57) ABSTRACT

A transfer printing paper is provided. The transfer printing paper includes a release layer and a conductive layer. The conductive layer is formed on the release layer and is suitable for being transferred to a flexible material layer. After being transferred to the flexible material layer, the conductive layer is configured to be electrically in contact with a wearer wearing the flexible material layer, so as to conduct a physiological signal of the wearer.

9 Claims, 3 Drawing Sheets

(56) References Cited

FOREIGN PATENT DOCUMENTS

| | | |
|---|---|---|
| WO | 2014025430 | 2/2014 |
| WO | 2015138515 | 9/2015 |

OTHER PUBLICATIONS

Wesley Taylor, "Technical Synopsis of Plasma Surface Treatment," Dec. 2009, Available at: http://www.iopp.org/files/public/taylorwesleyuflorida.pdf.

* cited by examiner

Before washed with water     After washed with water

Before washed with water

After washed with water

TRANSFER PRINTING PAPER AND MANUFACTURING METHOD OF SMART FABRIC

CROSS-REFERENCE TO RELATED APPLICATION

This application claims the priority benefit of Taiwan application serial no. 106134164, filed on Oct. 3, 2017. The entirety of the above-mentioned patent application is hereby incorporated by reference herein and made a part of this specification.

BACKGROUND

Technical Field

The disclosure relates to a transfer printing paper and a manufacturing method of a smart fabric. In particular, the disclosure relates to a transfer printing paper having a conductive layer and a manufacturing method of a smart fabric.

Description of Related Art

Generally, in order to obtain electrical physiological signals such as an electrocardiogram, an electroencephalogram, an electromyography signal, an electrode patch with conductive glue is required to be pasted to a test-taker's body for a long period of time, as such, measurement and recording may be performed by a measuring apparatus. Nevertheless, when the electrode patch is pasted for a long period of time, as the electrode patch is less breathable, sweat and vapors may not evaporate off the skin, and moreover, when the test-taker moves, the electrode patch may fall off easily owing to friction between the skin and the fabric. The test-taker may thus feel uncomfortable and inconvenient. In addition, the electrode patch is not environmentally friendly since the electrode patch may not be repeatedly used.

In recent years, as the textile technology advances, smart fabrics are manufactured from conductive fabrics or through printing circuits on fabrics or thin films. The smart fabrics are then further connected to physiological signal sensors for replacing the electrode patches. Nevertheless, the smart fabrics are fabrics of standard sizes which are largely manufactured, and thus, a wearer may not find a size which fits his/her body well. Further, when the wearer wears the fabric which poorly fits his/her body, as the fabric is not well-fitted to the wearer's skin, the problem of unstable signals may exist in the physiological signals measured.

SUMMARY

The disclosure provides a transfer printing paper capable of transferring a conductive layer to a flexible material layer, so as to manufacture a fabric for performing physiological signal detection.

The disclosure further provides a manufacturing method of a smart fabric in which a conductive layer is transferred to a fabric through simple steps, so as to manufacture a fabric for physiological signal detection.

A transfer printing paper of the disclosure includes a release layer and a conductive layer. The conductive layer is formed on the release layer and is suitable for being transferred to a flexible material layer. After being transferred to the flexible material layer, the conductive layer is configured to be electrically in contact with a wearer wearing the flexible material layer, so as to conduct a physiological signal of the wearer.

In an embodiment of the disclosure, the transfer printing paper is a thermal transfer printing paper.

In an embodiment of the disclosure, the conductive layer includes a conductive ink having extensibility.

In an embodiment of the disclosure, the conductive ink having extensibility further includes hydrophilic synthetic resin or hydrophilic solvent.

In an embodiment of the disclosure, the conductive layer is in direct contact with the wearer wearing the flexible material layer.

In an embodiment of the disclosure, a first protection layer is further included, wherein the first protection layer is disposed between the release layer and the conductive layer, and the first protection layer is in direct contact with the wearer wearing the flexible material layer.

In an embodiment of the disclosure, the first protection layer has conductivity and washability.

In an embodiment of the disclosure, a second protection layer is further included, wherein the conductive layer is disposed between the second protection layer and the release layer.

In an embodiment of the disclosure, stretchability of the second protection layer is greater than stretchability of the conductive layer.

In an embodiment of the disclosure, the release layer is treated with surface plasma.

A manufacturing method of a smart fabric provided by the disclosure includes following steps. A transfer printing paper is placed on a flexible material layer. The transfer printing paper includes a release layer and a conductive layer, wherein the conductive layer is formed on the release layer. The release layer is removed and the conductive layer is transferred to the flexible material layer, wherein the conductive layer is configured to conduct a physiological signal of a wearer wearing the flexible material layer.

In an embodiment of the disclosure, the method of transferring the conductive layer to the flexible material layer includes thermal transferring.

In an embodiment of the disclosure, a transferring temperature ranges from 160° C. to 200° C., and a transferring time ranges from 1 minute to 15 minutes.

In an embodiment of the disclosure, the transfer printing paper further includes a first protection layer, and the first protection layer is disposed between the release layer and the conductive layer.

In an embodiment of the disclosure, the step further includes forming the first protection layer on the conductive layer after transferring the conductive layer.

In an embodiment of the disclosure, the transfer printing paper further includes a second protection layer, and the conductive layer is disposed between the second protection layer and the release layer.

In an embodiment of the disclosure, the step further includes forming the second protection layer on the flexible material layer before transferring the conductive layer.

In an embodiment of the disclosure, the step further includes connecting the conductive layer to a physiological signal sensor through a conduction element after transferring the conductive layer.

In an embodiment of the disclosure, the step further includes processing the release layer with surface plasma.

In an embodiment of the disclosure, the conductive layer includes a conductive ink, and the conductive ink further includes hydrophilic synthetic resin or hydrophilic solvent.

To sum up, in the embodiments of the disclosure, the wearer may transfer the conductive layer of the transfer printing paper to the fabric through simple steps, so as to easily manufacture the small fabric which fits the body of the wearer well. In this way, when the conductive layer on the smart fabric is further connected to the physiological signal sensor for performing physiological signal detection, as the conductive layer is attached to the part of the wearer to be measured, stable and accurate physiological signals are thus obtained.

To make the aforementioned and other features and advantages of the disclosure more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the disclosure.

DESCRIPTION OF THE EMBODIMENTS

Figure 1:
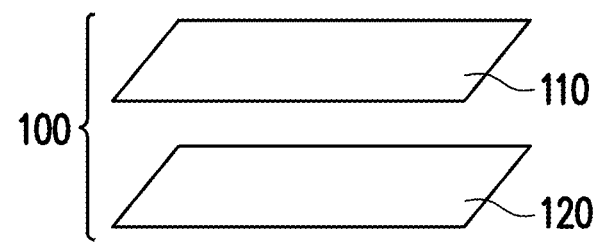
FIG. 1 is a schematic view of a transfer printing paper according to an exemplary embodiment.
Figure 1:

It should be understood that the foregoing and other detailed descriptions, features, and effects are intended to be described more comprehensively by providing embodiments accompanied with drawings hereinafter. In the following embodiments, wording used to indicate directions, such as "up," "down," "front," "back," "left," and "right," merely refers to directions in the accompanying drawings. Therefore, the directional wording is used to illustrate rather than limit the disclosure. Moreover, the same or similar reference numerals represent the same or similar elements in the following embodiments.

FIG. 1 is a schematic view of a transfer printing paper according to an exemplary embodiment. In this embodiment, a transfer printing paper 100 includes a release layer 110 and a conductive layer 120. In this embodiment, a material of the release layer 110 includes a material of high surface tension, such as a silicon-containing and easy-to-release material or thermoplastic polyurethane (TPU), polyurethane (PU), teflon, polyproylene (PP), polyethylene (PE), etc.

The conductive layer 120 is formed on the release layer 110. In this embodiment, the conductive layer 120 is a conductive pattern formed by, for example, a conductive ink. The conductive pattern may have a regular shape such as a circle, an oblong, and a rectangle, a loop pattern formed by wrapping a coil, or other irregular shapes, but the disclosure is not limited thereto. The conductive ink has, for example, extensibility and may be formed by conductive nonmetal such as carbon, conductive metal such as gold, silver, copper, aluminum, iron, and platinum, or a conductive polymer. The conductive metal may include conductive nano-metal with a size (e.g., a diameter) ranging from, for example, 0.1 nm to 1000 nm. In this embodiment, the conductive layer 120 is formed by, for example, printing such as screen printing or lithographic printing, transfer printing, or other suitable methods.

The release layer 110 including the material of high surface tension is conducive to pattern transferring in this embodiment. Nevertheless, most of the materials of high surface tension are hydrophobic and thus are not suitable for conductive ink printing. Therefore, a surface processing is further performed to the release layer 110 before the conductive layer 120 is formed on the release layer 110, so as to reduce the surface tension of the release layer 110 (such as elevating surface hydrophilicity of the release layer 110). Specifically, the surface processing to the release layer 110 may be performed by using atmospheric plasma, oxygen plasma, or argon plasma, so as to achieve purposes such as cleaning, increasing surface roughness, surface activation, or lowering surface tension. As such, the conductive ink may be printed on the hydrophobic release layer 110. In an embodiment, the conductive ink may further include hydrophilic synthetic resin or hydrophilic solvent, so as to decrease the surface tension of the release layer 110 (such as elevating surface hydrophilicity of the release layer 110). The hydrophilic synthetic resin is, for example, water-soluble polyester resin, water-soluble polyurethane resin, or water-soluble polyethylene oxide resin, etc., and the hydrophilic solvent is, for example, ethanol, glycerine, or ethylene glycol, etc.

The conductive layer 120 is adapted to be transferred to the flexible material layer 102. After being transferred to the flexible material layer 102, the conductive layer 120 is configured to be electrically in contact with a wearer wearing the flexible material layer 102, so as to conduct a physiological signal of the wearer. Specifically, in this embodiment, when the wearer wears the flexible material layer 102 with a transferred conductive layer 120, the conductive layer 120 is, for example, a film layer in direct contact with the skin of the wearer. As such, the physiological signal of the wearer may be conducted to a conduction element (not shown) electrically connected to the conductive layer 120 and a physiological signal sensor (not shown). The flexible material layer 102 may be a flexible thin film or cloth, wherein the cloth may be woven cloth, knitted fabric, non-woven fabric, fiber web, etc. of any kinds. Specifically, the flexible material layer 102 may be clothing, such as a garment, a pair of trousers, a leg cover, an oversleeve, a glove, a sock, a headgear, a sanitary mask, an eye mask, a hat, a scarf, a vest, suspenders, etc. or may be a protective gear such as a knee pad, a waist protection belt, a should support, a support belt, etc. Particularly, the flexible material layer 102 may be fitted clothes originally owned by the wearer, and that the clothes properly fit the wearer's body.

In this embodiment, the transfer printing paper 100 may be, for example, a thermal transfer printing paper. As such, the transfer printing paper 100 may further includes a functional film layer of a conventional thermal transfer printing paper, such as a hot melt adhesive layer. Similarly, when the transfer printing paper 100 is a transfer printing paper of another type, the transfer printing paper 100 may also include a film which is usually contained in such type of transfer printing paper.

Figure 2:
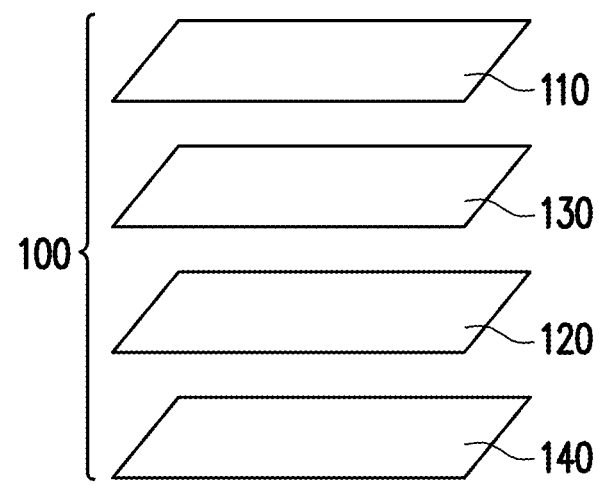
FIG. 2 is a schematic view of a transfer printing paper according to an exemplary embodiment.
Figure 2:
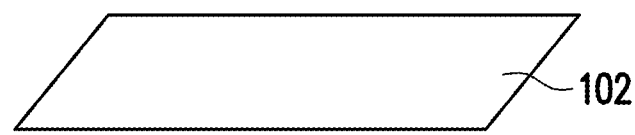

FIG. 2 is a schematic view of a transfer printing paper according to an exemplary embodiment. A difference between a transfer printing paper of FIG. 2 and the transfer printing paper of FIG. 1 are described as follows, and other identical films may be referred to as those described in the previous embodiment. Thus, details thereof are not repeated hereinafter. In this embodiment, the transfer printing paper 100 includes the release layer 110, the conductive layer 120, and at least one of a first protection layer 130 and a second protection layer 140. The transfer printing paper 100 is exemplified to include both the first protection layer 130 and the second protection layer 140 in this embodiment, but the disclosure is not limited thereto. In other embodiments, the transfer printing paper 100 may only include the first protection layer 130 or the second protection layer 140.

In this embodiment, the first protection layer 130 is, for example, disposed between the release layer 110 and the conductive layer 120, so as to protect the conductive layer 120 and electrically connect to the conductive layer 120. In addition, as the first protection layer 130 is exposed to the outside and is in contact with the skin, as such, the first protection layer 130 has washability and flexibility for the consideration of water-washing cleanliness and comfort. Specifically, when the wearer wears the flexible material layer 102 with a transferred conductive layer 120, the first protection layer 130 is, for example, a film layer in direct contact with the skin of the wearer. That is to say, the physiological signal of the wearer may be conducted to the conductive layer 120 through the first protection layer 130 and is further conducted to the conduction element electrically connected to the conductive layer 120 through the conductive layer 120. In this embodiment, a material of the first protection layer 130 includes, for example, carbon, polyamide or polyester conductive polymer, or carbon nanotube. The first protection layer 130 is formed by, for example, transfer printing, printing, foiling, laminating, or thermal pressing.

In this embodiment, the second protection layer 140 is, for example, disposed between the flexible material layer 102 and the conductive layer 120, and the conductive layer 120 is disposed between the second protection layer 140 and the release layer 110. In this embodiment, stretchability of the second protection layer 140 is, for example, greater than a stretchability of the conductive layer 120, so as to enhance stretching strength of the conductive layer 120. The second protection layer 140 may be a conductive or non-conductive material with stretchability. The second protection layer 140 includes, for example, a polymer such as TPU, PE, and PP, a non-woven fabric, or a carbon layer. The second protection layer 140 is formed by, for example, transfer printing, printing, foiling, laminating, or thermal pressing.

In this embodiment, through further forming the first protection layer 130 and the second protection layer 140, the conductive layer 120 is not only properly protected, conductivity of the conductive layer 120 is also maintained or strengthened, washability and flexibility of the conductive layer 120 are enhanced, and stretchability of the conductive layer 120 is increased. As such, the wearer may feel more comfortable and a service life of the conductive layer 120 is prolonged.

Figure 3:
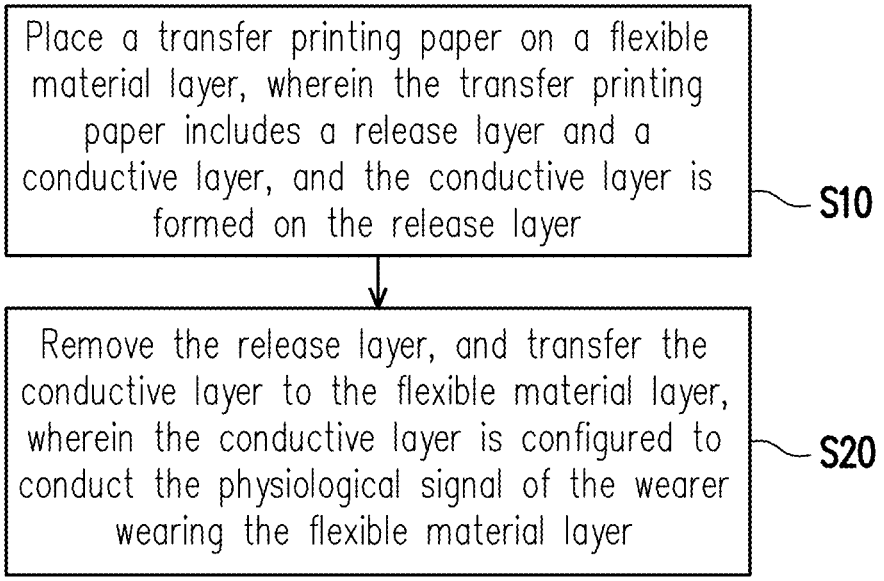
FIG. 3 is a schematic view of a manufacturing method of a smart fabric according to an exemplary embodiment.

A method of manufacturing a smart fabric using the foregoing transfer printing paper is described as follows. FIG. 3 is a schematic view of a manufacturing method of a smart fabric according to an exemplary embodiment.

Referring to FIG. 3, step S10 is performed first, and a transfer printing paper 100 is placed on a flexible material layer 102. The transfer printing paper 100 includes a release layer 110 and a conductive layer 120, wherein the conductive layer 120 is formed on the release layer 110. Specifically, the conductive layer 120 is placed to face the flexible material layer 102, and in this way, the conductive layer 120 is positioned on a specific area of the flexible material layer 102. In this embodiment, the specific area corresponds to a skin area providing a physiological signal of a wearer, wherein the physiological signal may be a signal such as an electrical physiological signal, an electronystagmogram, an electroencephalogram, or an electromyography signal. In this embodiment, the transfer printing paper 100 of FIG. 1 is taken as an example for illustration, but the disclosure is not limited thereto. In other embodiments, the transfer printing paper 100 may also be the transfer printing paper 100 of FIG. 2 or other transfer printing paper with the conductive layer described in the disclosure.

Next, step S20 is performed, and the release layer 110 is removed. The conductive layer 120 is transferred to the flexible material layer 102, wherein the conductive layer 120 is configured to conduct the physiological signal of the wearer wearing the flexible material layer 102. In this embodiment, a method of transferring the conductive layer 120 to the flexible material layer 102 includes thermal transferring, wherein a transferring temperature ranges from 160° C. to 200° C., and a transferring time ranges from 1 minute to 15 minutes. Specifically, the thermal transferring is performed through, for example, a thermal pressing device such as an iron or a heating device such as a hair dryer. In an embodiment, before the conductive layer 120 is transferred, a pre-processing process performed to the flexible material layer 102 may be further included. In the pre-processing process, a second protection layer 140 may be formed on the flexible material layer 102, and then, after the conductive layer 120 is transferred, the second protection layer 140 is located between the conductive layer 120 and the flexible material layer 102. Alternatively, in an embodiment, after the conductive layer 120 is transferred to the flexible material layer 102, a first protection layer 130 may be further formed on the conductive layer 120. In this way, the first protection layer 130 covers the conductive layer 120 and is a film layer in contact with the wearer's skin. A material and a forming method of the first protection layer 130 and the second protection layer 140 may be referred to as those described in the previous descriptions. Thus, details thereof are not repeated hereinafter.

Figure 4:
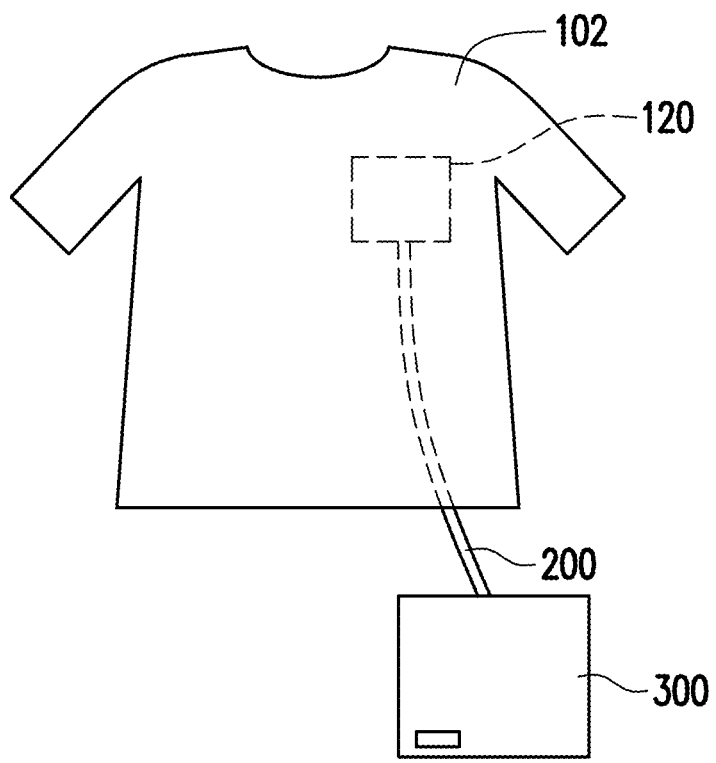
FIG. 4 is a schematic view of a physiological signal sensing module according to an exemplary embodiment.

FIG. 4 is a schematic view of a physiological signal sensing module according to an exemplary embodiment. Referring to FIG. 4, in this embodiment, a physiological signal sensing module includes a flexible material layer 102 to which a conductive layer 120 is transferred, a conduction element 200, and a physiological signal sensor 300. The conduction element 200 is, for example, an electric wire, and in another embodiment, a portion of the conduction element 200 may also be formed through the conductive layer 120. The physiological signal sensor 300 is a device with functions such as recording, analyzing, etc., so as to process the physiological signal. Specifically, after a test-taker wears the flexible material layer 102 to which the conductive layer 120 is transferred, the conductive layer 120 is connected to the physiological signal sensor 300 through the conduction element 200, and that the physiological signal of the test-taker may be detected. Note that in this embodiment, the transfer printing paper 100 of FIG. 1 is used for transferring and is taken as an example for illustration, but the disclosure is not limited thereto. In other embodiments, the flexible material layer 102 to which the conductive layer 120 is transferred may also be the flexible material layer 102 transferred through the transfer printing paper 100 shown in FIG. 2 or through the transfer printing paper having the conductive layer described in the embodiments of the disclosure.

The features of the disclosure are more specifically described in the following with reference to the Experimental Example. Although the following experimental example is described, the materials used and the amount and ratio thereof, as well as handling details and handling process, etc., can be suitably modified without exceeding the scope of the disclosure. Accordingly, restrictive interpretation should not be made to the disclosure based on the experimental example described below.

EXPERIMENTAL EXAMPLE

Performance of the fabric provided by the foregoing embodiments to which the conductive layer is transferred in a fastness to laundering test is described in detail through the Experimental Example. Information of the materials and equipment used in the Experimental Example is shown as follows.

Fabric: A fitted top provided by a test-taker himself/herself.

Water washing test machine: Model number W1420UW, purchased from TECO Electric and Machinery Co., Ltd.

Heart rate signal sensor: Model number BC1, purchased from Kinpo Electronics, Inc.

<Manufacturing of Transfer Printing Paper>

The conductive ink is printed on the release layer so as to form the conductive layer.

<Transferring Transfer Printing Paper to Fabric>

The conductive layer of the transfer printing paper is transferred to a specific position of the fabric by using an iron, wherein the specific position corresponds to the heart position of the test-taker.

<Test of Fastness to Laundering>

The test of fastness to laundering is performed according to the AATCC 135 test method.

Testing steps: First, a temperature of the water washing test machine (model number W1420UW, purchased from TECO Electric and Machinery Co., Ltd.) is set to be 27° C. (±3° C.). Next, the fabric with a transferred conductive layer is placed in the water washing test machine, 20 (operating for 240 minutes) and 100 (operating for 1200 minutes) wash and spin cycles are performed under the set temperature of 27° C. (±3° C.), and the fabric with a transferred conductive layer is then removed and dried.

<Appearance of Transferred Fabric>

Figure 5:
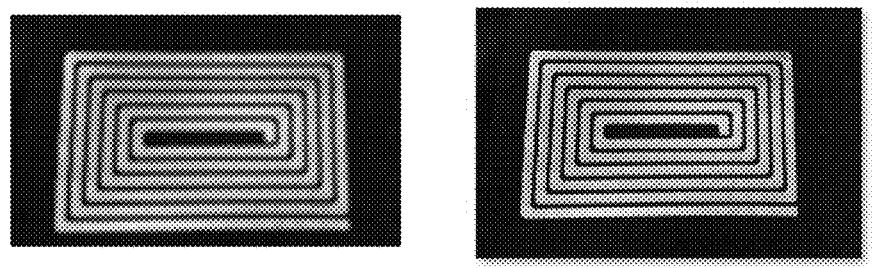
FIG. 5 are photos of a fabric with a transferred conductive layer before washed with water and after washed with water for 100 times according to an exemplary embodiment.

The fabric with a transferred conductive layer before washed with water and after washed with water for 100 times are respectively photographed, and results are shown in FIG. 5.

In FIG. 5, the appearance of the conductive layer of the fabric with a transferred conductive layer shows no sign of deformation on the printed appearance compared to the photo of the fabric before washed with water. It thus can be seen that the fabric with a transferred conductive layer has launderability.

<Testing of Surface Resistance and Signal Ratio>

Surface resistances and signal-to-noise ratios of the conductive layer transferred to the fabric before washed with water, after washed with water for 20 times, and after washed with water for 100 times are respectively measured. Test results are respectively shown in Table 1.

| Number of Times of Water Washing | Surface Resistance (ohm) | Signal-to-Noise Ratio |
|---|---|---|
| Not Water Washed (before washed with water) | 3.13 | 20.23 |
| 20 Times of Water Washing | 4.12 | 20.03 |
| 100 Times of Water Washing | 4.76 | 20.11 |

In Table 1, it can be seen that the conductive layer has both characteristics of low surface resistance values and stable signal-to-noise ratios before and after washed with water. Therefore, the fabric with a transferred conductive layer has launderability.

<Physiological Signal Measurement of Test-Taker Wearing Fabric>

When the test-taker wears the fabric before and after the fabric is water washed respectively for 20 times, the conductive layer of the fabric is connected to the heart rate signal sensor, so as to respectively measure the heart rates of the test-taker. Measurement results are shown in FIG. 6.

Figure 6:
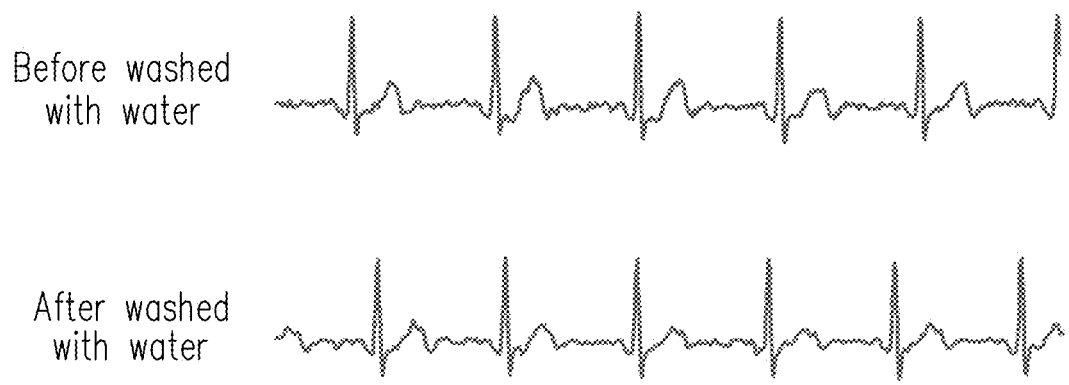
FIG. 6 are heart rate charts of a test-taker wearing a fabric with a transferred conductive layer before being washed and after being washed for 20 times according to an exemplary embodiment.

In FIG. 6, it can be seen that when the test-taker wears the fabric with a transferred conductive layer before and after the fabric is water washed for 20 times, the heart rates of the test-taker are similar, and the signals of the heart rates of the test-taker are stable as well. Therefore, the fabric with a transferred conductive layer has launderability and may be repeatedly used.

In view of the foregoing, the transfer printing paper provided by the embodiments of the disclosure is suitable for transferring the conductive layer to the flexible material layer. As such, the conductive layer may be transferred to the fitted fabric which properly fits the wearer's body by simple means such as ironing, and that the smart fabric which well fits the wearer may be easily manufactured. In this way, when the wearer wears the smart fabric, as the conductive layer is attached to the part of the wearer to be measured, stable and accurate physiological signals are thus obtained. In addition, the protection layers may be formed above and below the conductive layer, and that conductivity of the conductive layer is protected and moreover, the goals of providing enhanced-conductivity, comfort, flexibility, and launderability as well as repeated usage are thereby achieved. Therefore, comparing to the conventional electrode patches, the conductive layer transferred to the fabric is well-fitted and breathable and furthermore does not fall off easily. The test-taker feels comfortable and thus is more willing to take the physiological signal test for a long time.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. A manufacturing method of a smart fabric, comprising:
   placing a transfer printing sheet on a flexible fabric layer, the transfer printing sheet comprising:
   a release layer, wherein the release layer was processed with surface plasma; and
   a conductive layer formed on the release layer; and
   removing the release layer and transferring the conductive layer to the flexible fabric layer, wherein the conductive layer is configured to conduct a physiological signal of a wearer when the wearer is wearing the flexible fabric layer.

2. The manufacturing method of the smart fabric as claimed in claim 1, wherein the method of transferring the conductive layer to the flexible fabric layer comprises thermal transferring.

3. The manufacturing method of the smart fabric as claimed in claim 2, wherein a transferring temperature ranges from 160° C. to 200° C., and a transferring time ranges from 1 minute to 15 minutes.

4. The manufacturing method of the smart fabric as claimed in claim 1, wherein the transfer printing sheet further comprises a first protection layer, and the first protection layer is disposed between the release layer and the conductive layer.

5. The manufacturing method of the smart fabric as claimed in claim 1, further comprising forming a first protection layer on the conductive layer after transferring the conductive layer.

6. The manufacturing method of the smart fabric as claimed in claim 1, wherein the transfer printing sheet further comprises a second protection layer, and the conductive layer is disposed between the second protection layer and the release layer.

7. The manufacturing method of the smart fabric as claimed in claim 1, further comprising forming a second protection layer on the flexible fabric layer before transferring the conductive layer.

8. The manufacturing method of the smart fabric as claimed in claim 1, further comprising connecting the conductive layer to a physiological signal sensor through a conduction element after transferring the conductive layer.

9. The manufacturing method of the smart fabric as claimed in claim 1, wherein the conductive layer is formed by using a conductive ink, and the conductive ink further comprises hydrophilic synthetic resin or hydrophilic solvent.

\* \* \* \* \*